(12) United States Patent
Han et al.

(10) Patent No.: US 11,247,195 B2
(45) Date of Patent: Feb. 15, 2022

(54) METHOD OF PREPARING CATALYST FOR OXIDATIVE DEHYDROGENATION AND METHOD OF PERFORMING OXIDATIVE DEHYDROGENATION USING CATALYST

(71) Applicant: LG CHEM, LTD., Seoul (KR)

(72) Inventors: Sang Jin Han, Daejeon (KR); Dong Hyun Ko, Daejeon (KR); Kyong Yong Cha, Daejeon (KR); Jun Kyu Han, Daejeon (KR); Sun Hwan Hwang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 561 days.

(21) Appl. No.: 16/307,676

(22) PCT Filed: Apr. 26, 2018

(86) PCT No.: PCT/KR2018/004832
§ 371 (c)(1),
(2) Date: Dec. 6, 2018

(87) PCT Pub. No.: WO2018/203615
PCT Pub. Date: Nov. 8, 2018

(65) Prior Publication Data
US 2019/0299193 A1 Oct. 3, 2019

(30) Foreign Application Priority Data

May 4, 2017 (KR) .................. 10-2017-0056741
Apr. 25, 2018 (KR) .................. 10-2018-0047836

(51) Int. Cl.
*B01J 23/60* (2006.01)
*B01J 23/80* (2006.01)
(Continued)

(52) U.S. Cl.
CPC ............ *B01J 23/80* (2013.01); *B01J 23/005* (2013.01); *B01J 35/002* (2013.01); *B01J 37/03* (2013.01);
(Continued)

(58) Field of Classification Search
CPC ........ B01J 23/80; B01J 23/005; B01J 35/002; B01J 37/03; B01J 37/031; B01J 37/04;
(Continued)

(56) References Cited

U.S. PATENT DOCUMENTS 2,483,771 A 10/1949 Holder
3,822,210 A 7/1974 Iwase et al.
(Continued)

FOREIGN PATENT DOCUMENTS

CN 1040015 2/1990
CN 101674883 3/2010
(Continued)

OTHER PUBLICATIONS

Machine translation of CN-103740365-A (Year: 2014).*
(Continued)

*Primary Examiner* — Haytham Soliman
(74) *Attorney, Agent, or Firm* — Dentons US LLP

(57) ABSTRACT

A method of preparing a catalyst for oxidative dehydrogenation that includes coprecipitation and injecting inert gas or air at a specific time point to reduce the ratio of an inactive $\alpha\text{-}Fe_2O_3$ crystal structure, thereby improving the activity of the catalyst. Also provided is a method of performing oxidative dehydrogenation using the catalyst. When oxidative dehydrogenation of butene is performed using the catalyst, side reaction may be reduced, and selectivity for butadiene may be improved, providing butadiene with high productivity.

10 Claims, 3 Drawing Sheets

(51) Int. Cl.
| | |
|---|---|
| *B01J 35/00* | (2006.01) |
| *B01J 37/03* | (2006.01) |
| *C01G 49/06* | (2006.01) |
| *C07C 5/48* | (2006.01) |
| *C07C 11/167* | (2006.01) |
| *C01G 49/00* | (2006.01) |
| *C01B 13/36* | (2006.01) |
| *B01J 23/00* | (2006.01) |
| *B01J 37/04* | (2006.01) |
| *B01J 23/76* | (2006.01) |

(52) U.S. Cl.
CPC ............ *B01J 37/031* (2013.01); *B01J 37/04* (2013.01); *C01B 13/363* (2013.01); *C01G 49/0063* (2013.01); *C01G 49/06* (2013.01); *C07C 5/48* (2013.01); *C07C 11/167* (2013.01); *B01J 23/76* (2013.01); *B01J 2219/00166* (2013.01); *C01P 2002/72* (2013.01); *C01P 2004/51* (2013.01); *C01P 2004/61* (2013.01); *C07C 2523/745* (2013.01); *C07C 2523/76* (2013.01); *C07C 2523/78* (2013.01); *C07C 2523/80* (2013.01)

(58) Field of Classification Search
CPC .. B01J 23/76; B01J 2219/00166; B01J 23/78; B01J 37/009; B01J 37/08; C01B 13/363; C01G 49/0063; C01G 49/06; C01P 2002/72; C01P 2004/51; C01P 2004/61; C07C 2523/745; C07C 2523/76; C07C 2523/78; C07C 2523/90
USPC ....................................................... 502/329
See application file for complete search history.

(56) References Cited

U.S. PATENT DOCUMENTS

| 8,513,479 | B2 | 8/2013 | Chung et al. |
|---|---|---|---|
| 2004/0186016 | A1 | 9/2004 | Bog et al. |
| 2009/0312588 | A1 | 12/2009 | Hatscher et al. |
| 2010/0099936 | A1 | 4/2010 | Shin et al. |
| 2010/0121123 | A1* | 5/2010 | Chung ............... B01J 35/002 585/629 |
| 2011/0004041 | A1 | 1/2011 | Chung et al. |
| 2014/0070916 | A1 | 3/2014 | Odahara |

FOREIGN PATENT DOCUMENTS

| CN | 202893347 | | 4/2013 | |
|---|---|---|---|---|
| CN | 103740365 | A * | 4/2014 | |
| JP | S52-156192 | | 12/1977 | |
| JP | 2010094674 | | 4/2010 | |
| JP | 2010-534553 | | 11/2010 | |
| JP | 2013-538679 | | 10/2013 | |
| KR | 10-0847206 | | 7/2008 | |
| KR | 10-2009-0031760 | | 3/2009 | |
| KR | 10-2009-0034139 | | 4/2009 | |
| KR | 10-2011-0036290 | | 4/2011 | |
| KR | 10-1071230 | | 10/2011 | |
| KR | 10-1538877 | | 7/2015 | |
| KR | 10-2015-0093320 | | 8/2015 | |
| WO | 2008/140213 | | 11/2008 | |
| WO | 2009/045002 | | 4/2009 | |
| WO | 2012/030891 | | 3/2012 | |
| WO | WO-2017022762 | A1 * | 2/2017 | .......... H01M 8/1253 |

OTHER PUBLICATIONS

Karimipour et al., "Red luminescence of Zn /ZnO core-shell nanorods in a mixture of LTZA/Zinc acetate matrix: Study of the effects of Nitrogen bubbling, Cobalt doping and thioglycolic acid," Journal of Luminescence 178: 234-240 (2016).

Jiao, et al., "The Preparation of Nano ZnFe2O4 by Spraying Coprecipitation and its Structure Analysis," Chinese Journal of Organic Chemistry (2001) 17(5):631-635.

Chung, et al., "Factors Affect on the Reaction Performance of the Oxidative Dehydrogenation of n-Butene to 1,3-Butadiene Over Zn-Ferrite Catalyst," Catal Lett (2009) 130:417-423.

* cited by examiner

[FIG. 1]
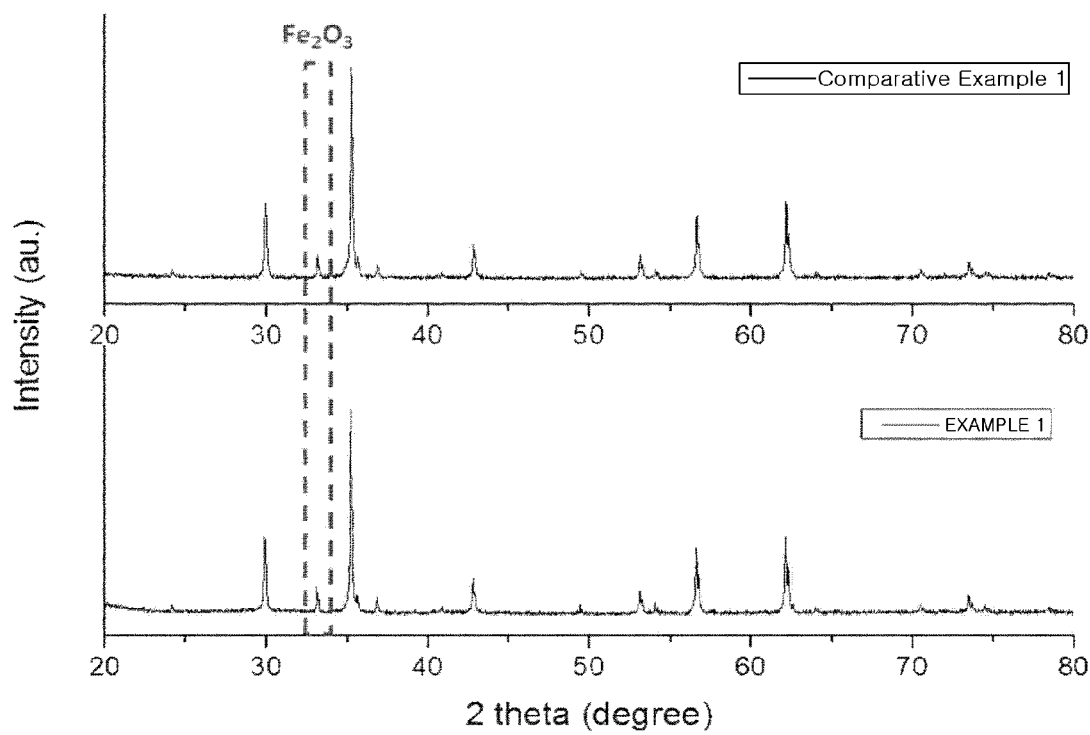

[FIG. 2]
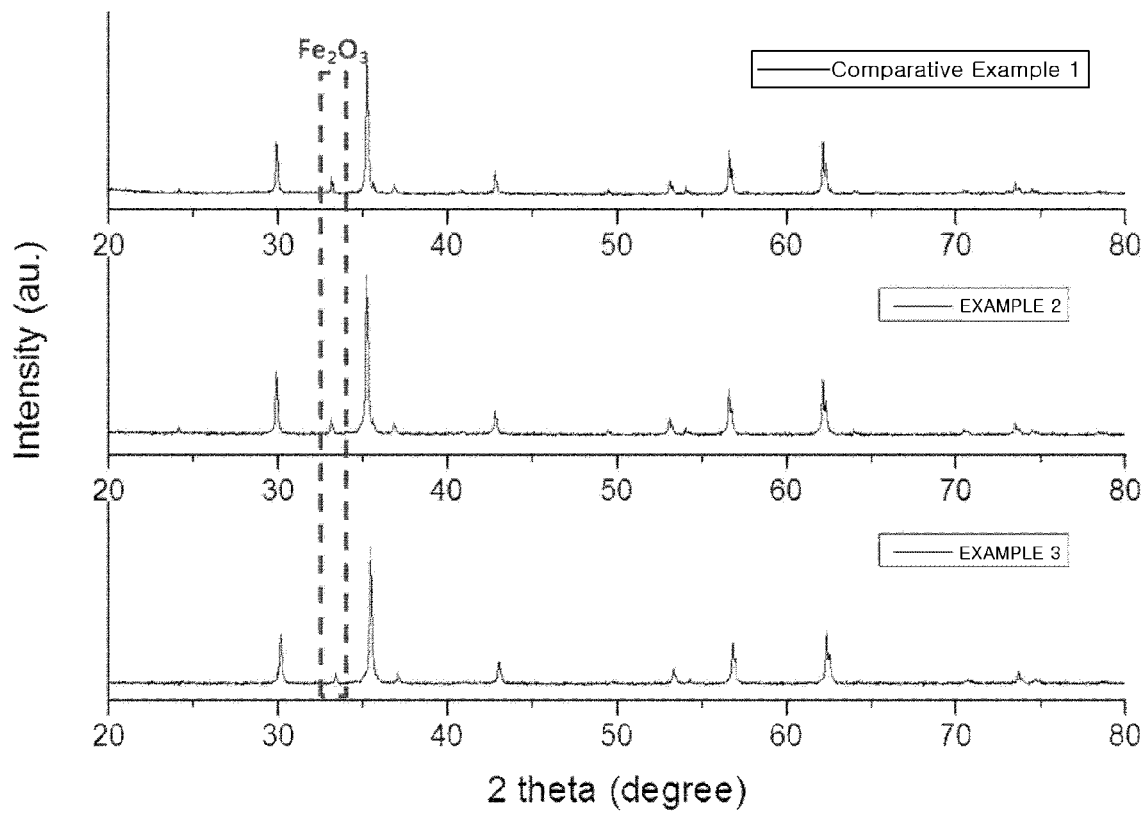

[FIG. 3]
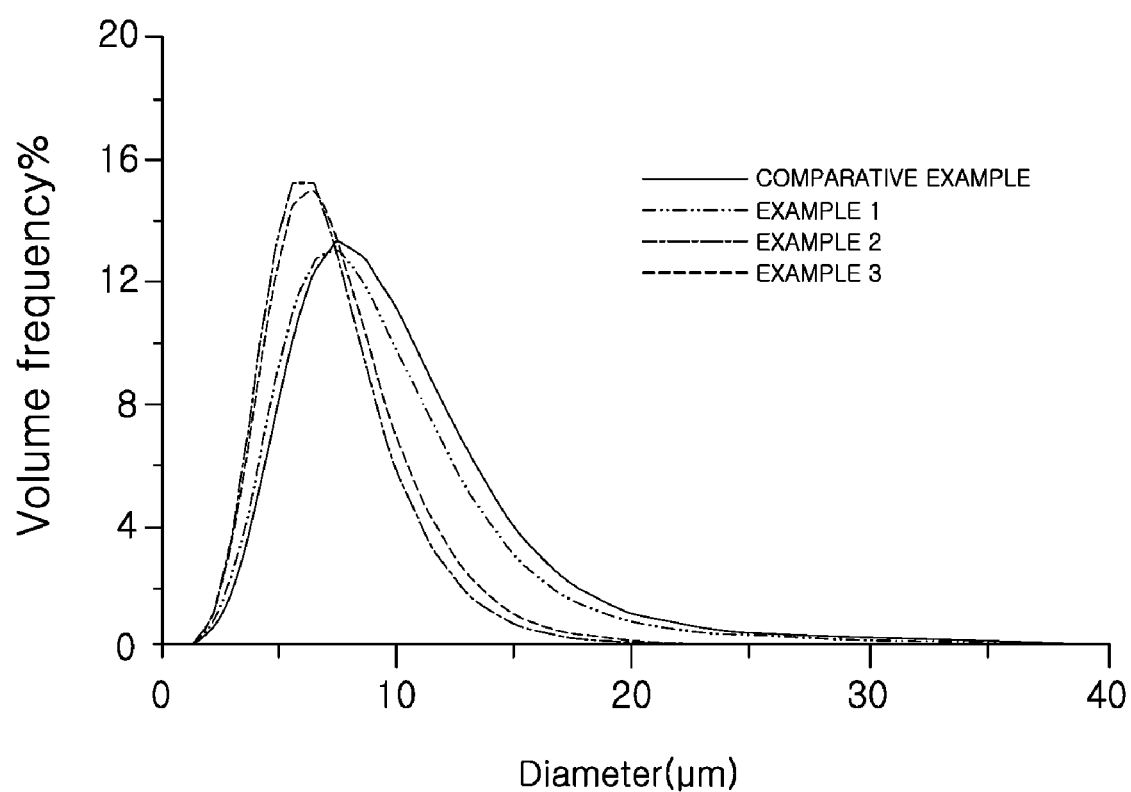

METHOD OF PREPARING CATALYST FOR OXIDATIVE DEHYDROGENATION AND METHOD OF PERFORMING OXIDATIVE DEHYDROGENATION USING CATALYST

CROSS-REFERENCE TO RELATED APPLICATIONS

This application is a National Stage Application of International Application No. PCT/KR2018/004832 filed on Apr. 26, 2018, which claims priority to Korean Patent Application No. 10-2017-0056741, filed on May 4, 2017, and Korean Patent Application No. 10-2018-0047836, re-filed on Apr. 25, 2018, based on the priority of the above patent, in the Korean Intellectual Property Office, the disclosures of each of which are incorporated herein by reference.

TECHNICAL FIELD

The present invention relates to a method of preparing a catalyst for oxidative dehydrogenation and a method of performing oxidative dehydrogenation using the catalyst. According to the method of preparing a catalyst for oxidative dehydrogenation, when a catalyst for oxidative dehydrogenation is prepared, the ratio of an inactive α-$Fe_2O_3$ crystal structure is reduced, so that the prepared catalyst may have high activity. In addition, when the prepared catalyst is used to prepare butadiene, side reaction may be reduced, and selectivity for butadiene may be improved, thereby increasing butadiene productivity.

BACKGROUND ART 1,3-butadiene, a major basic product of petroleum fraction, is a representative raw material used in preparation of synthetic rubber, and the price thereof fluctuates rapidly in connection with supply and demand of the petrochemical industry. Examples of the method of preparing 1,3-butadiene include naphtha cracking, direct dehydrogenation of normal butene, oxidative dehydrogenation of normal butene, and the like. According to the method of preparing 1,3-butadiene by oxidative dehydrogenation of normal butene, butene and oxygen react in the presence of a metal oxide catalyst to generate 1,3-butadiene and water. In this case, water generated as a result of the reaction is stable. Thus, the method is thermodynamically very advantageous. In addition, since oxidative dehydrogenation of normal butene is an exothermic reaction unlike direct dehydrogenation, reaction may be performed at a low temperature. Thus, 1,3-butadiene may be obtained in high yield while reducing energy consumption. In addition, in the case of oxidative dehydrogenation, since an oxidizing agent is added, generation of carbon deposits which shorten the catalyst life by poisoning the catalyst is reduced. Further, since removal of the oxidizing agent is easy, the method of preparing 1,3-butadiene using oxidative dehydrogenation is very suitable for commercialization.

In general, a ferrite catalyst widely known as a catalyst for oxidative dehydrogenation of butene is synthesized by a coprecipitation method. A catalyst synthesized by the coprecipitation method exists as an active crystal structure and an inactive $Fe_2O_3$ crystal structure during oxidative dehydrogenation. Therefore, there has been demand for a technique for reducing the ratio of an inactive $Fe_2O_3$ crystal structure during catalyst synthesis, or for preparing a catalyst having excellent activity even though an inactive crystal structure is present in a certain amount or more.

In addition, when a catalyst is prepared using a coprecipitation method, due to technical and spatial constraints, the amount of catalyst prepared in a single manufacturing process is small. Thus, to achieve the required amount of catalyst, the same manufacturing process must be repeated several times. This makes it difficult to improve productivity. To overcome such a problem, a method of concentrating a catalyst during catalyst synthesis has been used. However, in this case, the ratio of an inactive crystal structure is increased, and the activity and stability of the prepared catalyst may be lowered.

PRIOR ART DOCUMENTS

Patent Documents

KR 10-0847206 B1
KR 10-1071230 B1

DISCLOSURE

Technical Problem

Therefore, the present invention has been made in view of the above problems, and it is one object of the present invention to provide a method of preparing a catalyst for oxidative dehydrogenation. According to the method of preparing a catalyst for oxidative dehydrogenation, a catalyst exhibiting excellent activity in oxidative dehydrogenation even though an inactive $Fe_2O_3$ crystal structure is present in a certain level may be provided. In addition, the ratio of an inactive $Fe_2O_3$ crystal structure may be reduced even in a preparation process in which a coprecipitation method is used.

It is another object of the present invention to provide a method of performing oxidative dehydrogenation using the catalyst prepared using the method of preparing a catalyst for oxidative dehydrogenation. According to the method of performing oxidative dehydrogenation using the catalyst, when oxidative dehydrogenation is performed, side reaction may be reduced, and butadiene yield or selectivity for butadiene may be significantly improved.

The above and other objects can be accomplished by the present disclosure described below.

Technical Solution

In accordance with one aspect of the present invention, provided is a method of preparing a catalyst for oxidative dehydrogenation including a step of preparing an aqueous metal precursor solution by adding a trivalent cationic iron (Fe) precursor and a divalent cationic metal (A) precursor to water; a step of coprecipitating iron and the metal (A) by adding the aqueous metal precursor solution and the basic aqueous solution to a coprecipitation bath containing an aqueous solution having a pH of 6 or more or water; and a step of performing burning of the coprecipitated coprecipitate, wherein a process of supplying inert gas or air to the coprecipitation bath is performed during the coprecipitation step; after completion of the coprecipitation step; or from during the coprecipitation step until after completion of the coprecipitation step.

In accordance with another aspect of the present invention, provided is a method of performing oxidative dehydrogenation, including a step, in which oxidative dehydrogenation is performed by passing reactants including oxygen and a C4 mixture containing normal butene through a reactor filled with the catalyst for oxidative dehydrogenation according to the preparation method.

Advantageous Effects

As apparent from the foregoing, the present invention advantageously provides a method of preparing a catalyst for oxidative dehydrogenation and a method of performing oxidative dehydrogenation using the catalyst. According to the present invention, when a catalyst for oxidative dehydrogenation is prepared using a coprecipitation method, a process of injecting inert gas or air into a coprecipitation bath at a specific time point is performed to improve the activity of the catalyst. Optionally, when an aqueous metal precursor solution is supplied through the lower part of the coprecipitation bath, the ratio of an inactive $Fe_2O_3$ crystal structure in the catalyst is reduced to further improve catalytic activity. In addition, when oxidative dehydrogenation of butene is performed using the prepared catalyst, side reaction can be reduced, and selectivity for butadiene and butadiene yield can be improved. Therefore, the present invention can provide high-quality butadiene with high productivity.

DESCRIPTION OF DRAWINGS

FIG. 1 is XRD data showing the crystal structures of the zinc ferrite catalysts prepared according to Example 1 (air supply) and Comparative Example 1 (conventional synthesis method).

FIG. 2 is XRD data showing the crystal structures of the zinc ferrite catalysts prepared according to Example 2 ($N_2$ supply+aqueous metal precursor solution, supply through lower part), Example 3 (air supply+aqueous metal precursor solution, supply through lower part), and Comparative Example 1 (conventional synthesis method).

FIG. 3 is a graph showing the particle size distributions of the coprecipitate slurries prepared according to Examples 1 to 3 and Comparative Example 1.

BEST MODE

Hereinafter, the method of preparing a catalyst for oxidative dehydrogenation according to the present invention will be described in detail.

The present inventors confirmed that, when a ferrite catalyst was synthesized using a coprecipitation method, an inactive $Fe_2O_3$ crystal structure capable of affecting the activity of a catalyst for oxidative dehydrogenation was generated. The present inventors investigated a method capable of increasing catalytic activity during oxidative dehydrogenation even when an inactive $Fe_2O_3$ crystal structure was present in a certain amount or more and a method capable of reducing the ratio of the inactive crystal structure. As a result, the present inventors confirmed that, when a step of supplying nitrogen ($N_2$) gas or air to a coprecipitation solution at a specific time point during catalyst synthesis was performed, and optionally when an aqueous metal precursor solution was supplied through the lower part of a coprecipitation bath in a coprecipitation step, the degree of dispersion of a coprecipitate corresponding to a ferrite catalyst precursor was maximized, and the ratio of the inactive $Fe_2O_3$ crystal structure in the ferrite catalyst was reduced. Accordingly, the present inventors confirmed that the above-described problems were solved when the method of the present invention was used, and completed the present invention based thereon.

For example, the method of preparing a catalyst for oxidative dehydrogenation according to the present invention includes a step of preparing an aqueous metal precursor solution by adding a trivalent cationic iron (Fe) precursor and a divalent cationic metal (A) precursor to water; a step of coprecipitating iron and the metal (A) by adding the aqueous metal precursor solution and the basic aqueous solution to a coprecipitation bath containing an aqueous solution having a pH of 6 or more or water; and a step of performing burning of the coprecipitated coprecipitate, wherein a process of supplying inert gas or air to the coprecipitation bath is performed during the coprecipitation step; after completion of the coprecipitation step; or from during the coprecipitation step until after completion of the coprecipitation step.

For example, the process of supplying inert gas or air to the coprecipitation bath may be a process of supplying inert gas or air into a coprecipitation bath while agitating a solution in the coprecipitation bath using an agitating means such as an impeller, a process of connecting a pipe to the lower part of a coprecipitation bath and supplying inert gas or air into a coprecipitation bath through the pipe, or a process of providing a tube, e.g., a Teflon tube, in a coprecipitation bath and supplying inert gas or air into a solution through the tube. In addition, the pipe and tube may have an inner diameter of, for example, 1/8" to 1/2" or 1/6" to 1/2", and locations thereof are not particularly limited so long as the pipe and tube are located in the lower part of a coprecipitation bath, that is, below the surface of a solution in the coprecipitation bath. For example, the pipe and tube may be located at the lower part of the coprecipitation bath, specifically within a half of the distance from the bottom of the coprecipitation bath to the surface of the solution.

Hereinafter, the method of preparing a catalyst for oxidative dehydrogenation will be described in detail stepwise.

For example, in the step of preparing an aqueous metal precursor solution, a trivalent cationic iron (Fe) precursor and a divalent cationic metal (A) precursor may be independently one or more selected from a nitrate, an ammonium salt, a sulfate, and a chloride. Preferably, the precursors may be independently a nitrate or chloride in consideration of the manufacturing costs and ease of purchase, which are required for mass production.

For example, the divalent cationic metal (A) may be one or more selected from the group consisting of copper (Cu), radium (Ra), barium (Ba), strontium (Sr), calcium (Ca), beryllium (Be), zinc (Zn), magnesium (Mg), manganese (Mn), and cobalt (Co), preferably zinc (Zn) or manganese (Mn), which exhibits high activity in oxidative dehydrogenation of butene, most preferably zinc (Zn) in terms of butadiene yield or selectivity for butadiene.

The trivalent cationic iron (Fe) precursor and the divalent cationic metal (A) precursor are mixed in water to prepare an aqueous solution. When the metal precursor is dissolved in water and is present in a liquid phase, ion exchange between iron and the divalent cationic metal is easy, so that the desired coprecipitate may be easily obtained.

For example, the water may be distilled water.

In general, the mixing ratio of the trivalent cationic iron (Fe) precursor and the divalent cationic metal (A) precursor in the aqueous metal precursor solution is preferably 1.5 to 10 mol, 1.5 to 4 mol, or 1.5 to 2.5 mol of the trivalent cationic iron (Fe) precursor to 1 mol of the divalent cationic metal (A) precursor. Within this range, formation of an active crystal structure in oxidative dehydrogenation is facilitated and catalytic activity may be improved.

In addition, the aqueous metal precursor solution may have a pH of, for example, 0 to 4, 1 to 3, or 1 to 2. Within this range, a desired active ingredient may be stably formed.

After the aqueous metal precursor solution is prepared, a coprecipitation bath containing an aqueous solution having a pH of 6 or more or water for coprecipitating iron and the metal (A) is prepared, and the aqueous metal precursor solution is added to the coprecipitation bath to coprecipitate iron and the metal (A).

For example, in the coprecipitation step, the aqueous solution having a pH of 6 or more may be one or more selected from an aqueous solution of sodium hydroxide and aqueous ammonia. When the pH of the coprecipitation bath is adjusted to 6 or more, 6 to 10, or 7 to 8 before the aqueous metal precursor solution is added dropwise to the coprecipitation bath, the width of the initial pH change due to addition of the aqueous metal precursor solution is reduced, and thus a catalyst having a uniform composition may be stably formed.

For example, in the method of preparing a catalyst of the present invention, a process of injecting inert gas or air into the coprecipitation bath during the coprecipitation step may be performed. By performing the process, oxygen and the metal precursor may be uniformly combined, increasing mixing effect, thereby improving the reaction activity of oxidative dehydrogenation. For example, when the catalyst prepared according to the present invention is used to perform oxidative dehydrogenation of butene, the conversion rate of butene, selectivity for butadiene, and butadiene yield may be improved, and generation of side reaction products may be reduced. In addition, there is an advantage of exhibiting excellent reaction activity at a relatively low hot spot temperature.

In the present invention, the hot spot refers to the portion having the highest temperature in the catalyst bed loaded in the reactor during the reaction.

The conditions for injecting the inert gas or air into the coprecipitation bath are not particularly limited. For example, the inert gas or air may be injected into the coprecipitation bath at a speed of 0.1 to 2 L/min or 0.5 to 1 L/min based on the volume of the solution in the coprecipitation bath for 1 to 300 minutes, 10 to 200 minutes, 30 to 100 minutes, or 40 to 90 minutes. Within this range, a catalyst having a small particle size and a uniform particle size distribution may be prepared, and the ratio of an active crystal structure may be increased.

For example, in the coprecipitation step, the pH of the coprecipitation solution is preferably maintained at 7 to 10 or 7 to 8. Within this range, the activity or stability of the catalyst may be excellent. Therefore, in the coprecipitation step, the basic aqueous solution and the aqueous metal precursor solution are preferably simultaneously added for the purpose of maintaining the pH at 7 to 10.

For example, in the coprecipitation step, the aqueous metal precursor solution and the basic aqueous solution may be added dropwise together to the coprecipitation bath to coprecipitate iron and the metal (A). For example, the basic aqueous solution may be one or more selected from sodium hydroxide and aqueous ammonia.

In the present invention, 'dropwise adding' means that two or more solutions are added dropwise to the same point or container. The 'same point' includes a range from the dropping point to the point where the dropped solution is splashed on the surface of the existing solution, or a range from the dropping point to the point where the dropped solution goes down to the surface of the existing solution while maintaining properties thereof without being mixed with the existing solution.

As another example, in the coprecipitation step, the aqueous metal precursor solution may be supplied through the lower part of the coprecipitation bath and the basic aqueous solution may be added dropwise to the coprecipitation bath to coprecipitate iron and the metal (A). When the aqueous metal precursor solution is directly fed into the coprecipitation bath separately from the basic aqueous solution, the speed of the metal precursor diffusing into the solution provided in the coprecipitation bath is increased. Thus, a uniform crystal structure may be formed, and the ratio of an inactive crystal structure may be reduced, so that a catalyst exhibiting high activity may be provided.

In the present invention, a method of supplying the aqueous metal precursor solution into the coprecipitation bath is not particularly limited so long as the aqueous metal precursor solution is directly introduced below the surface of the solution in the coprecipitation bath without being introduced to the surface of the solution in the coprecipitation bath. For example, the aqueous metal precursor solution may be supplied through a pipe connected to the lower part of the coprecipitation bath, or through a tube provided so that one end thereof is immersed in the solution in the coprecipitation bath. In this case, since the aqueous metal precursor solution is supplied through the lower part of the coprecipitation bath, the speed of the metal precursor diffusing into the solution may be increased.

For example, the coprecipitate is in the slurry state in the coprecipitation bath. The slurry particles may have a median size of 7 μm or less or 1 to 7 μm and a mode size of 7 μm or less or 1 to 7 μm. Within this range, butadiene may be obtained in a high yield compared to a conventional zinc ferrite catalyst.

In the present invention, the median size and mode size of the slurry particles are measured using a Laser Particle Size Analyzer-960 (Horiba, Co., Ltd.). The refractive index required for the measurement is set on the basis of the most abundant iron (Fe) in the slurry state.

Before burning of the coprecipitate obtained from the coprecipitation solution prepared in the coprecipitation step is performed, a step of agitating, aging, or agitating and aging the coprecipitation solution may be performed. In this case, a sufficient amount of the coprecipitate may be obtained.

For example, in the method of preparing a catalyst according to the present invention, after completion of the coprecipitation step, a process of supplying inert gas or air while agitating the coprecipitation solution may be performed. In this case, the prepared catalyst may exhibit excellent activity in oxidative dehydrogenation. For example, when the catalyst is used to perform oxidative dehydrogenation of butene, the conversion rate of butene and selectivity for butadiene may be improved, and generation of side reaction products may be reduced. In addition, there is an advantage of exhibiting excellent reaction activity at a relatively low hot spot temperature.

As another example, in the method of preparing a catalyst according to the present invention, during the step of coprecipitating the added aqueous metal precursor solution and basic aqueous solution, a process of injecting inert gas or air into the coprecipitation bath may be performed. After completion of the coprecipitation step, a process of additionally injecting inert gas or air into the coprecipitation bath while agitating the coprecipitation solution may be performed. In this case, the catalyst may exhibit excellent activity in oxidative dehydrogenation.

As another example, in the method of preparing a catalyst according to the present invention, a process of continuously injecting inert gas or air into the coprecipitation bath from the coprecipitation step, in which the aqueous metal precursor solution and the basic aqueous solution are added to the coprecipitation bath and coprecipitated, to the step of agitating the coprecipitation solution after completion of the coprecipitation step, may be performed. That is, a process of continuously injecting inert gas or air into the coprecipitation bath from the coprecipitation step to completion of the coprecipitation step may be performed. In this case, the catalyst may exhibit excellent activity in oxidative dehydrogenation.

For example, the inert gas may be nitrogen ($N_2$).

For example, the agitating and aging may be independently performed for 30 minutes to 3 hours or 30 minutes to 2 hours, without being limited thereto.

The coprecipitate may be obtained by drying, filtering, or drying and filtering the coprecipitation solution. The catalyst including an $AFe_2O_4$ crystal structure may be obtained by burning the coprecipitate.

The drying method and filtering method are not particularly limited so long as the methods are conventionally used in the art. For example, the filtering process may be performed using vacuum filtration. When necessary, after completion of the filtering process, a washing process may be performed.

For example, the drying process may be performed at 60 to 100° C., 70 to 100° C., or 80 to 100° C. for 12 to 20 hours, 14 to 20 hours, or 14 to 18 hours using a conventional dryer.

For example, the burning process may be performed at 400 to 800° C., 500 to 800° C., or 550 to 750° C. for 1 to 10 hours, 3 to 8 hours, or 5 to 7 hours using a conventional burning furnace, without being limited thereto.

The catalyst obtained through the burning process may include an $AFe_2O_4$ crystal structure. As a specific example, the catalyst may exhibit mixed phases including an $AFe_2O_4$ crystal structure and an $\alpha\text{-}Fe_2O_3$ crystal structure.

For example, the catalyst obtained according to one embodiment of the present invention may include 93.7% by weight or more, 94.0% by weight or more, 94.5% by weight or more, 94.8% by weight or more, or 94.8 to 96.0% by weight of an $AFe_2O_4$ crystal structure; and 6.3% by weight or less, 6.0% by weight or less, 5.5% by weight or less, 5.2% by weight or less, or 4.0 to 5.2% by weight of an $\alpha\text{-}Fe_2O_3$ crystal structure.

In the present invention, the weight ratio of $AFe_2O_4$ to $\alpha\text{-}Fe_2O_3$ may be calculated from the intensity of an $AFe_2O_4$ peak (2theta: 29.5 to 30.5°, 34.5 to 35.5°, 42 to 43°, 52.5 to 53.5°, 56.5 to 57.5°, 62 to 63°) and the intensity of an $\alpha\text{-}Fe_2O_3a$ peak (2theta: 33 to 34°) in XRD diffraction analysis.

In addition, in XRD diffraction analysis, as diffraction peaks by the plane on which each peak exists, $AFe_2O_4$ peaks exist at (220), (311), (222), (400), (422), (511), and (440) positions, and an $\alpha\text{-}Fe_2O_3$ peak exists at a (104) position.

As a specific example, the method of preparing a catalyst according to the present invention includes 1) a step of preparing an aqueous metal precursor solution by adding a trivalent cationic iron (Fe) precursor and a divalent cationic metal (A) precursor to water; 2) a step of coprecipitating iron and the metal (A) by adding the aqueous metal precursor solution and a basic aqueous solution dropwise to a coprecipitation bath containing an aqueous solution having a pH of 6 to 10 or water; and 3) a step of agitating, or agitating and aging a coprecipitation solution obtained in the coprecipitation step and performing burning of a coprecipitated coprecipitate, wherein a process of injecting nitrogen or air into the coprecipitation bath is performed during the coprecipitation step and the agitating step.

As another specific example, the method of preparing a catalyst according to the present invention includes 1) a step of preparing an aqueous metal precursor solution by adding a trivalent cationic iron (Fe) precursor and a divalent cationic metal (A) precursor to water; 2) a step of coprecipitating iron and the metal (A) by supplying the aqueous metal precursor solution through the lower part of a coprecipitation bath containing an aqueous solution having a pH of 6 to 10 or water while adding a basic aqueous solution dropwise to the coprecipitation bath; and 3) a step of agitating, or agitating and aging a coprecipitation solution obtained in the coprecipitation step and performing burning of a coprecipitated coprecipitate, wherein a process of injecting nitrogen or air into the coprecipitation bath is performed during the coprecipitation step and the agitating step.

In addition, the catalyst prepared according to the method of the present invention satisfies Equation 1 below:

$$0 \leq T2/T1 \leq 0.80, \quad \text{[Equation 1]}$$

wherein T2 represents a content of an $\alpha\text{-}Fe_2O_3$ crystal structure contained in the catalyst prepared according to the method of preparing a catalyst according to the present invention, which includes a step of supplying an aqueous metal precursor solution to the lower part of a coprecipitation bath and injecting inert gas or air, based on 100% by weight of the total amount of the catalyst; T1 represents a content of an $\alpha\text{-}Fe_2O_3$ crystal structure contained in the catalyst prepared in the same manner as in the method of preparing a catalyst, except that an aqueous metal precursor solution and a basic aqueous solution are added dropwise to coprecipitate, and the process of injecting inert gas or air is omitted, based on 100% by weight of the total amount of the catalyst; and the content of the $\alpha\text{-}Fe_2O_3$ crystal structure is determined by measuring the intensity of a peak (2theta: 33 to 34°) corresponding to the $\alpha\text{-}Fe_2O_3$ crystal structure in XRD diffraction analysis of the catalyst.

More preferably, T2/T1 may be 0 to 0.75, 0 to 0.70, or 0 to 0.68. Within this range, the catalyst may have excellent activity. In addition, when the catalyst is used to perform oxidative dehydrogenation, butadiene yield or selectivity for butadiene may be improved, high-quality butadiene may be provided with high productivity, and the catalyst may exhibit excellent reaction activity at a relatively low hot spot temperature.

The catalyst for oxidative dehydrogenation prepared according to the present invention may be used to perform oxidative dehydrogenation of butene to obtain butadiene. Hereinafter, the method of performing oxidative dehydrogenation according to the present invention will described.

For example, the method of performing oxidative dehydrogenation according to the present invention may include a step in which oxidative dehydrogenation is performed by passing reactants including oxygen and a C4 mixture containing normal butene through a reactor filled with the catalyst for oxidative dehydrogenation according to the preparation method.

For example, the method of performing oxidative dehydrogenation may be a method of preparing butadiene.

As a specific example, the method of preparing butadiene according to the present invention may include i) a step of filling a reactor with a catalyst for oxidative dehydrogenation; and ii) a step, in which oxidative dehydrogenation is performed by continuously passing reactants including oxygen and a C4 mixture containing normal butene through the catalyst layer of a reactor filled with the catalyst.

For example, the C4 mixture includes one or more selected from normal butene isomers including 2-butene (trans-2-butene and cis-2-butene) and 1-butene, and may optionally further include normal butane or C4 raffinate-3.

The reactants may further include one or more selected from air, nitrogen, steam, and carbon dioxide.

As a specific example, the reactants may include a C4 mixture, oxygen, steam, and nitrogen in a molar ratio of 1:0.01 to 1.5:1 to 15:1 to 10 or 1:0.5 to 1.2:5 to 15:1 to 10. Within this range, reaction heat may be easily controlled, and butadiene yield may be improved.

For example, the oxidative dehydrogenation reaction may be performed at a reaction temperature of 250 to 430° C., 300 to 425° C., or 350 to 425° C. Within this range, reaction efficiency may be improved without significantly increasing energy consumption, and thus the productivity of butadiene may be increased and the activity and safety of the catalyst may be increased.

For example, the oxidative dehydrogenation reaction may be performed at a gas hourly space velocity (GHSV) of 50 to 2,000 $h^{-1}$, 50 to 1,500 $h^{-1}$, or 50 to 1,000 $h^{-1}$ based on normal butene. Within this range, reaction efficiency is excellent, and thus conversion rate, selectivity, and yield may be excellent.

Hereinafter, the present invention will be described in more detail with reference to the following preferred examples. However, these examples are provided for illustrative purposes only and should not be construed as limiting the scope and spirit of the present invention. In addition, it will be apparent to those skilled in the art that various changes and modifications may be made without departing from the spirit and scope of the present invention, and such changes and modifications are also within the scope of the appended claims.

EXAMPLES

Example 1

0.122 mol of zinc chloride ($ZnCl_2$) and 0.243 mol of ferric chloride ($FeCl_3 6H_2O$) were dissolved in 12.778 mol of water to prepare an aqueous metal precursor solution. In this case, the mole ratio of Fe to Zn, which were metal components contained in the aqueous metal precursor solution, was 2:1.

Then, the aqueous metal precursor solution and 9 to 10% by weight of aqueous ammonia were added dropwise to a coprecipitation bath containing distilled water to coprecipitate iron and zinc while nitrogen is supplied. In this case, nitrogen was supplied at an injection rate of 1 L/min based on 1 liter of the distilled water for 80 to 90 minutes. After completion of coprecipitation, the coprecipitation solution was agitated for 1 hour so that sufficient coprecipitation could be achieved. In this case, nitrogen was supplied at an injection rate of 0.5 L/min based on 1 liter of the distilled water. Thereafter, agitation was stopped, and the coprecipitation solution was allowed to stand at room temperature for 1 hour to precipitate all precipitates. That is, an aging process for preparing a coprecipitate was performed.

The coprecipitation solution after agitation and aging was vacuum-filtered using a vacuum filter to obtain a coprecipitate. The obtained coprecipitate was washed, followed by drying at 90° C. for 24 hours. The dried coprecipitate was put into a burning furnace and heat-treated at 650° C. for 5 hours to prepare a zinc ferrite catalyst.

Comparative Example 1

The same procedures as in Example 1 were performed, except that the process of feeding nitrogen into a coprecipitation bath was omitted.

Test Example

The following test analysis was performed using the zinc ferrite catalysts prepared according to Example 1 and Comparative Example 1.

Test Example 1: XRD Analysis

XRD analysis was performed to confirm the crystal structures of the catalysts prepared according to Example 1 and Comparative Example 1 and the ratio of the crystal structures. The analysis results are shown in FIG. 1 and Table 1 below.

TABLE 1

| Classification | Example 1 | Comparative Example 1 |
|---|---|---|
| $ZnFe_2O_4$ crystal structure (% by weight) | 96.0 | 92.4 |
| $\alpha$-$Fe_2O_3$ crystal structure (% by weight) | 4.0 | 7.6 |

Referring to FIG. 1 and Table 1, the zinc ferrite catalysts prepared according to Example 1 and Comparative Example 1 exhibit mixed phases including a $ZnFe_2O_4$ crystal structure and an $\alpha$-$Fe_2O_3$ crystal structure. In the case of the catalyst according to Example 1, the ratio of the $\alpha$-$Fe_2O_3$ crystal structure is considerably low. Based on these results, it can be seen that supply of nitrogen gas in the coprecipitation bath has a favorable influence on the crystal structure of the ferrite-based catalyst.

Test Example 2: Oxidative Dehydrogenation

Oxidative dehydrogenation was performed using the zinc ferrite catalysts prepared according to Example 1 and Comparative Example 1 to prepare butadiene. Results for Examples 1a to 1c and Comparative Examples 1a to 1d are shown in Table 2 below.

The catalyst prepared according to Example 1 or Comparative Example 1 was fixed to a catalyst bed at a volume of 30 cc in a metal tubular reactor having a diameter of 1.8 cm, and 2-butene mixtures containing 40% by weight of cis-2-butene and 60% by weight of trans-2-butene and oxygen as reactants were fed into the reactor, and then nitrogen and steam were introduced into the reactor. In the reactants, the molar ratios of oxygen/butene, steam/butene, and nitrogen/butene were set to 1, 8, and 1, respectively. Steam generated by vaporization of water in a vaporizer at 340° C. was introduced into the reactor with the reactants.

The feeding rate of butene mixtures was set to 0.625 cc/min using a mass flow rate controller for liquid, the feeding rate of oxygen and nitrogen was controlled using a mass flow rate controller for gas, and the feeding rate of steam was controlled using a liquid pump. In the reactor, wherein gas hourly space velocity (GHSV) was set to 66 $h^{-1}$, reaction was performed under atmospheric pressure (pressure gauge being 0) and the temperature conditions shown in Table 2 below.

After completion of reaction, products were analyzed using gas chromatography (GC). In the mixtures, the conversion rate of butene (BE_Conv.), selectivity for 1,3-butadiene (S_BD), 1,3-butadiene yield (Y), selectivity for COx (S_COx), selectivity for heavy components (S heavy), and the conversion rate of $O_2$ ($O_2$_Conv.) were calculated according to Equations 2 to 4 below, respectively. To measured hot spot temperature, a thermocouple (ThermoCouple; TC) was connected to a transfer device and moved from the top of the reactor to the bottom of the reactor at a constant speed while performing scanning.

Conversion rate (%)=(Number of moles of butene or oxygen reacted/number of moles of butene or oxygen supplied)×100  [Equation 2]

Selectivity (%)=(Number of moles of 1,3-butadiene, COx or heavy components generated/number of moles of butene reacted)×100  [Equation 3]

Butadiene Yield (%)=(Number of moles of 1,3-butadiene generated/number of moles of butene supplied)×100  [Equation 4]

TABLE 2

| Classification | Reaction temperature (° C.) | BE_Conv. (%) | S_BD (%) | Y (%) | S_COx (%) | S_heavy (%) | $O_2$_Conv. (%) | Hot spot temperature (° C.) |
|---|---|---|---|---|---|---|---|---|
| Example 1a | 330 | 83.2 | 89.5 | 74.4 | 9.5 | 1.0 | 96.4 | 475 |
| Example 1b | 334 | 85.4 | 89.7 | 76.6 | 9.2 | 1.1 | 99.0 | — |
| Example 1c | 335 | 85.5 | 89.2 | 76.3 | 9.9 | 1.0 | 99.6 | 476 |
| Comparative Example 1a | 325 | 79.7 | 88.5 | 70.6 | 10.5 | 1.0 | 95.3 | 478 |
| Comparative Example 1b | 330 | 82.8 | 88.8 | 73.5 | 10.3 | 1.0 | 97.8 | 484.9 |
| Comparative Example 1c | 334 | 84.1 | 88.5 | 74.4 | 10.5 | 1.0 | 99.9 | 485.8 |
| Comparative Example 1d | 335 | 83.7 | 89.6 | 75.0 | 9.4 | 1.0 | 99.2 | — |

Reaction conditions: GHSV 66 h$^{-1}$, oxygen:steam:nitrogen = 1:8:1 (based on number of moles of butene)

Referring to Table 2, in Example 1 and Comparative Example 1, the highest activity is observed under oxygen-rich conditions. In the case of Example 1, wherein a catalyst is prepared according to a method including a step of supplying nitrogen at a specific point of time, the conversion of butene, selectivity for butadiene, and butadiene yield are increased while selectivity for COx, a side reaction product, is reduced, compared to Comparative Example 1, wherein the step of supplying nitrogen is omitted. In addition, compared to the catalyst according to Comparative Example 1, the catalyst according to Example 1 exhibits excellent activity during oxidative dehydrogenation at low hot spot temperature. That is, it can be seen that, when the process of supplying nitrogen is introduced during synthesis of the zinc ferrite catalyst, the ratio of an inactive $\alpha$-$Fe_2O_3$ crystal structure is reduced and reaction activity is increased.

Example 2

An aqueous metal precursor solution was prepared according to the same conditions as in Example 1, and then the same procedures as in Example 1 were performed, except that the aqueous metal precursor solution was supplied through the lower part of a coprecipitation bath and aqueous ammonia was added dropwise to coprecipitate iron and zinc.

Example 3

The same procedures as in Example 2 were performed, except that air was supplied instead of nitrogen ($N_2$).

Test Example 3: XRD Analysis

XRD analysis was performed to confirm the crystal structures of the catalysts prepared according to Examples 1 to 3 and the ratio of the crystal structures. Also, XRD analysis for Comparative Example 1 was performed. The XRD analysis results are shown in FIG. 2 and Table 3 below.

TABLE 3

| Classification | Example 2 | Example 3 | Comparative Example 1 |
|---|---|---|---|
| $ZnFe_2O_4$ crystal structure (% by weight) | 95.3 | 94.8 | 92.4 |
| $\alpha$-$Fe_2O_3$ crystal structure (% by weight) | 4.7 | 5.2 | 7.6 |

Referring to FIG. 2 and Table 3, the zinc ferrites catalyst prepared according to Examples 2 and 3 exhibit mixed phases including a $ZnFe_2O_4$ crystal structure and an $\alpha$-$Fe_2O_3$ crystal structure. In the case of Examples 2 or 3, wherein a catalyst is prepared by a method including a step of supplying an aqueous metal precursor solution through the lower part of a coprecipitation bath and a step of supplying nitrogen or oxygen into the coprecipitation bath, the ratio of the $\alpha$-$Fe_2O_3$ crystal structure as an inactive crystal structure is reduced, compared to Comparative Example 1 not following the method of Examples 2 and 3. That is, when the step of supplying an aqueous metal precursor solution through the lower part of a coprecipitation bath and a step of supplying nitrogen gas or air are performed during synthesis of a zinc ferrite using a coprecipitation method, a zinc ferrite catalyst having a low ratio of an inactive crystal structure is prepared.

Test Example 4: Particle Size Analysis

The particle sizes of the ferrite catalyst precursor slurries prepared according to Examples 1 to 3 and Comparative Example 1 were analyzed, and the results are shown in Table 4 and FIG. 3 below. The particle size analysis was conducted using a Laser Particle Size Analyzer-960 (Horiba, Co., Ltd.).

At this time, a refractive index required for analysis was set based on Fe as a main component in the slurry.

TABLE 4

| Classification | Example 1 | Example 2 | Example 3 | Comparative Example 1 |
|---|---|---|---|---|
| Median size (μm) | 6.9 | 5.8 | 6.0 | 8.4 |
| Mode size (μm) | 7.2 | 6.2 | 6.3 | 8.3 |

* Median size: The diameter of the particles distributed in the middle
* Mode size: The diameter of the most distributed particles As shown in Table 4 and FIG. 3, compared to Comparative Example 1, in the case of Examples 1 to 3, slurry particles are relatively small and have a uniform particle size. In addition, compared to Example 1, in the case of Examples 2 and 3, slurry particles are relatively small and have a more uniform particle size. From these results, it can be seen that supply of nitrogen effectively enables the catalyst precursor to have a small and uniform particle size. In addition, it can be seen that supply of air and repositioning of supply of an aqueous metal precursor solution effectively enables the catalyst precursor to have a smaller and more uniform particle size.

Test Example 5: Oxidative Dehydrogenation

Oxidative dehydrogenation was performed using the zinc ferrite catalysts prepared according to Examples 2 and in the same manner and under the same conditions as described above to prepare butadiene. Results for Examples 2a to 2d and Examples 3a to 3c are shown in Table 5, and for comparison, the results for Comparative Examples 1a to 1d are re-described.

TABLE 5

| Classification | Reaction temperature (° C.) | BE_Conv. (%) | S_BD (%) | Y (%) | S_COx (%) | S_heavy (%) | $O_2$_Conv. (%) | Hot spot temperature (° C.) |
|---|---|---|---|---|---|---|---|---|
| Example 2a | 340 | 86.7 | 89.4 | 77.5 | 9.6 | 1.0 | 99.8 | — |
| Example 2b | 330 | 86.2 | 89.5 | 77.1 | 9.4 | 1.1 | 97.6 | 474.2 |
| Example 2c | 335 | 86.5 | 89.3 | 77.2 | 9.6 | 1.1 | 99.8 | 486.9 |
| Example 2d | 325 | 81.1 | 90.0 | 73.0 | 9.0 | 1.0 | 94.4 | 468.2 |
| Example 3a | 330 | 85.5 | 89.2 | 76.3 | 9.8 | 1.0 | 99.5 | — |
| Example 3b | 334 | 86.6 | 89.5 | 77.5 | 9.4 | 1.1 | 97.7 | 476.0 |
| Example 3c | 339 | 87.1 | 89.4 | 77.9 | 9.6 | 1.0 | 99.9 | 478.8 |
| Comparative Example 1a | 325 | 79.7 | 88.5 | 70.6 | 10.5 | 1.0 | 95.3 | 478 |
| Comparative Example 1b | 330 | 82.8 | 88.8 | 73.5 | 10.3 | 1.0 | 97.8 | 484.9 |
| Comparative Example 1c | 334 | 84.1 | 88.5 | 74.4 | 10.5 | 1.0 | 99.9 | 485.8 |
| Comparative Example 1d | 335 | 83.7 | 89.6 | 75.0 | 9.4 | 1.0 | 99.2 | — |

Reaction conditions: GHSV 66 h$^{-1}$, oxygen:steam:nitrogen = 1:8:1 (based on number of moles of butene)

Referring to Table 5, in Examples 2 and 3 and Comparative Example 1, it can be seen that, when oxidative dehydrogenation is performed, high catalytic activity is observed under conditions of high oxygen consumption. In the case of Examples 2 and 3, wherein oxidative dehydrogenation is performed using a zinc ferrite catalyst prepared by a method including a step of supplying an aqueous metal precursor solution through the lower part of a coprecipitation bath and a step of supplying nitrogen or air at a specific time point, compared to Comparative Example 1 not following the method of Examples 2 and 3, the conversion rate of butene, selectivity for butadiene, and butadiene yield are increased while selectivity for COx as a side reaction product is decreased. In addition, when the zinc ferrite catalysts of Examples 2 and 3 according to the present invention are used, compared to Comparative Example 1, reaction activity is excellent even at low hot spot temperature.

That is, in the case that a zinc ferrite catalyst is synthesized using a coprecipitation method, when an aqueous metal precursor solution is supplied through the lower part of a coprecipitation bath and nitrogen or air is supplied at a specific time point, the ratio of an inactive crystal structure in the zinc ferrite catalyst is reduced, and the activity of the catalyst is also increased.

The invention claimed is:

1. A method of preparing a catalyst for oxidative dehydrogenation, comprising:
   preparing an aqueous metal precursor solution by adding a trivalent cationic iron (Fe) precursor and a divalent cationic metal (A) precursor to water;
   coprecipitating iron and the metal (A) by adding the aqueous metal precursor solution and a basic aqueous solution to a coprecipitation bath containing an aqueous solution having a pH of 6 or more or water while agitating the aqueous solution or water in the coprecipitation bath and injecting nitrogen as an inert gas through a tube or pipe located below the surface of the aqueous solution or water in the coprecipitation bath to form a coprecipitate and a coprecipitation solution; and
   burning the coprecipitate to yield the catalyst, wherein during coprecipitating, the aqueous metal precursor solution is supplied beneath the surface of the aqueous solution or water in the coprecipitation bath, and wherein the injecting nitrogen to the coprecipitation bath is performed at a speed of 0.1 to 2 L/min.

2. The method according to claim 1, wherein the method further comprises aging the coprecipitation solution formed during coprecipitating.

3. The method according to claim 1, wherein the trivalent cationic iron (Fe) precursor and the divalent cationic metal (A) precursor are independently one or more selected from the group consisting of a nitrate, an ammonium salt, a sulfate, and a chloride.

4. The method according to claim 1, wherein the divalent cationic metal (A) is one or more metals selected from the group consisting of copper (Cu), radium (Ra), barium (Ba), strontium (Sr), calcium (Ca), beryllium (Be), zinc (Zn), magnesium (Mg), manganese (Mn), and cobalt (Co).

5. The method according to claim 1, wherein a pH of the coprecipitation solution is maintained at 7 to 10 during coprecipitating.

6. The method according to claim 1, wherein the catalyst comprises an $AFe_2O_4$ crystal structure.

7. The method according to claim 1, wherein the catalyst exhibits mixed phases comprising an $AFe_2O_4$ crystal structure and an $\alpha\text{-}Fe_2O_3$ crystal structure.

8. The method according to claim 1, wherein the coprecipitate is obtained by drying, filtering, or drying and filtering the coprecipitation solution.

9. The method according to claim 7, wherein the catalyst satisfies Equation 1:

$$0 \leq T2/T1 \leq 0.80, \quad \text{Equation 1}$$

wherein:
- T2 is an amount of an $\alpha\text{-}Fe_2O_3$ crystal structure contained in the catalyst based on 100% by weight of a total amount of the catalyst;
- T1 is an amount of an $\alpha\text{-}Fe_2O_3$ crystal structure contained in a catalyst prepared in an identical manner to that in the method of claim 7, except that the process of supplying nitrogen as an inert gas or air is omitted, based on 100% by weight of a total content of the catalyst; and
- the amount of the $\alpha\text{-}Fe_2O_3$ crystal structure is determined by measuring an intensity of a peak (2theta: 33 to 34°) corresponding to the $\alpha\text{-}Fe_2O_3$ crystal structure in an XRD diffraction analysis of the catalyst.

10. The method according to claim 1, further comprising injecting nitrogen to the coprecipitation bath after completion of coprecipitating.

* * * * *